(12) United States Patent
Moser et al.

(10) Patent No.: US 10,568,785 B2
(45) Date of Patent: Feb. 25, 2020

(54) PROTECTIVE COVER

(71) Applicant: MEDAXIS AG, Baar (CH)

(72) Inventors: Beat Moser, Uerzlikon (CH); Adrian Zweifel, Jona (CH); Oezkan Selek, Baar (CH); Beat Widmer, Lucerne (CH); Roman Good, Zurich (CH)

(73) Assignee: MEDAXIS AG, Baar (CH)

( * ) Notice: Subject to any disclaimer, the term of this patent is extended or adjusted under 35 U.S.C. 154(b) by 779 days.

(21) Appl. No.: 15/235,368

(22) Filed: Aug. 12, 2016

(65) Prior Publication Data

US 2017/0049641 A1 Feb. 23, 2017

(30) Foreign Application Priority Data

Aug. 21, 2015 (EP) .................................... 15182057

(51) Int. Cl.
*A61F 15/00* (2006.01)
*A61B 90/00* (2016.01)
(Continued)

(52) U.S. Cl.
CPC ............ *A61F 15/008* (2013.01); *A61B 46/23* (2016.02); *A61B 46/27* (2016.02); *A61B 90/05* (2016.02);
(Continued)

(58) Field of Classification Search
CPC .......... A61F 15/008; A61F 2013/00306; A61F 2013/00297; A61F 2013/00182;
(Continued)

(56) References Cited

U.S. PATENT DOCUMENTS 2,367,690 A * 1/1945 Purdy ................... A61F 15/006
128/888
2,448,938 A * 9/1948 Wayne ..................... A61J 13/00
604/346
(Continued)

FOREIGN PATENT DOCUMENTS

CN  2512719 Y  9/2002
CN  2663797     12/2004
(Continued)

OTHER PUBLICATIONS

European Patent Office; European Search Report issued in priority application No. 15182057.8, filed Aug. 21, 2015. dated Feb. 25, 2016.
(Continued)

*Primary Examiner* — Tarla R Patel
(74) *Attorney, Agent, or Firm* — Fishman Stewart PLLC (57) ABSTRACT

A protective cover for the protection against contamination from body and/or irrigation fluid during treatment of wounds/ulcers includes a first opening to be placed on a patient and a second opening for inserting a handpiece. The protective cover includes a fluid-tight and flexible hollow body that defines a treatment chamber having a shape that adapts to motion of a handpiece. The hollow body may include a stiffening element for keeping the first opening in an open state during treatment. Additionally, a device for the irrigation of wounds or ulcers, such as for debriding dead body tissue by way of a micro water jet, may include a hand-operated lance with a nozzle for producing an irrigation fluid jet, such as a micro water jet. The lance may be inserted through the second opening of the protective cover so that the nozzle is located within the treatment chamber of the protective cover.

18 Claims, 3 Drawing Sheets

(51) Int. Cl.

| | | |
|---|---|---|
| *A61B 46/23* | (2016.01) | |
| *A61B 90/40* | (2016.01) | |
| *A61B 46/27* | (2016.01) | |
| *A61M 3/02* | (2006.01) | |
| *A61F 13/00* | (2006.01) | |
| *A61B 17/3203* | (2006.01) | |
| *A61M 1/00* | (2006.01) | |

(52) U.S. Cl.
CPC ........... *A61B 90/40* (2016.02); *A61M 3/0279* (2013.01); *A61B 17/3203* (2013.01); *A61F 13/00068* (2013.01); *A61F 2013/00165* (2013.01); *A61F 2013/00182* (2013.01); *A61F 2013/00297* (2013.01); *A61F 2013/00306* (2013.01); *A61M 1/0058* (2013.01)

(58) Field of Classification Search
CPC ..... A61F 13/00068; A61F 2013/00165; A61B 46/27; A61B 90/05; A61B 90/40; A61B 46/23; A61B 17/3203; A61M 3/0279; A61M 1/0058

See application file for complete search history.

(56) References Cited

U.S. PATENT DOCUMENTS

| | | | | |
|---|---|---|---|---|
| 4,870,977 A * | 10/1989 | Imonti | ................ | A61F 15/008 |
| | | | | 128/890 |
| 4,998,538 A | 12/1991 | Charowsky | | |
| 5,224,940 A * | 7/1993 | Dann | ................ | A61B 90/05 |
| | | | | 604/187 |
| 5,248,307 A * | 9/1993 | Sokoloff | ................ | A61M 27/00 |
| | | | | 128/846 |
| 5,460,604 A | 10/1995 | Arnett et al. | | |
| 5,941,859 A * | 8/1999 | Lerman | ................ | A61M 27/00 |
| | | | | 604/289 |
| 6,156,004 A * | 12/2000 | Tremaine | ............ | A61M 1/0084 |
| | | | | 604/27 |
| 6,210,381 B1 * | 4/2001 | Morse | ................ | A61M 3/0279 |
| | | | | 604/289 |
| 6,274,787 B1 * | 8/2001 | Downing | ............. | A61F 15/008 |
| | | | | 602/14 |
| 6,402,724 B1 * | 6/2002 | Smith | ................ | A61M 3/0262 |
| | | | | 604/268 |
| 6,695,773 B1 | 2/2004 | Dahlinger | | |
| 7,540,860 B2 * | 6/2009 | Stamler | ............... | A61M 3/0262 |
| | | | | 604/268 |
| 7,909,805 B2 * | 3/2011 | Weston | ............... | A61M 1/0001 |
| | | | | 604/313 |
| 9,381,009 B2 * | 7/2016 | Leahy | ................ | A61B 17/0218 |
| 9,687,388 B2 * | 6/2017 | Raniere | .................. | A61F 13/14 |
| 9,925,361 B2 * | 3/2018 | Lin | ....................... | A61F 9/0026 |
| 2002/0161345 A1 * | 10/2002 | McMillin | ............... | A61M 35/00 |
| | | | | 604/304 |
| 2005/0222544 A1 * | 10/2005 | Weston | ............... | A61M 1/0001 |
| | | | | 604/313 |
| 2009/0126741 A1 | 5/2009 | Voic | | |
| 2009/0326489 A1 * | 12/2009 | Kensy | ................. | A61B 17/3203 |
| | | | | 604/319 |
| 2010/0036367 A1 * | 2/2010 | Krohn | ................. | A61M 1/0088 |
| | | | | 604/543 |
| 2011/0290257 A1 * | 12/2011 | Hillis | ..................... | A61B 90/40 |
| | | | | 128/847 |
| 2012/0010578 A1 * | 1/2012 | Hirsch | ................ | A61M 1/0058 |
| | | | | 604/290 |
| 2014/0060548 A1 * | 3/2014 | Check | ................... | A61F 15/008 |
| | | | | 128/845 |
| 2014/0207027 A1 * | 7/2014 | Navia | ............... | A61F 13/00068 |
| | | | | 601/6 |
| 2015/0011980 A1 * | 1/2015 | Tan | .................. | A61F 13/00068 |
| | | | | 604/544 |

FOREIGN PATENT DOCUMENTS

| | | | | |
|---|---|---|---|---|
| CN | 2843376 Y | 12/2006 | | |
| EP | 2251142 A1 | 11/2010 | | |
| JP | 2001-514041 A | 9/2001 | | |
| JP | 2009-542329 A | 12/2009 | | |
| JP | 2012-509110 A | 4/2012 | | |
| WO | WO-99/11192 A1 | 3/1999 | | |
| WO | WO-9911192 A1 * | 3/1999 | ......... | A61M 3/0262 |
| WO | WO-2008/005261 A2 | 1/2008 | | |
| WO | WO-2010/057208 A1 | 5/2010 | | |

OTHER PUBLICATIONS

Translation of Japanese Office Action, Application No. 2016-160514, dated Apr. 25, 2017.

Chinese Search Report, 201610693457.4, Application Date Aug. 19, 2016.

* cited by examiner

PROTECTIVE COVER

CROSS REFERENCE TO RELATED APPLICATIONS

This application claims the benefit of priority to European patent application No. 15182057.8, filed Aug. 21, 2015, which is incorporated herein by reference in its entirety as though fully set forth herein.

TECHNICAL FIELD

The present invention relates to a protective cover for the protection against contamination from body and/or irrigation fluid during the treatment of wounds or ulcers. It further relates to a device equipped with such a protective cover for irrigating wounds or ulcers.

BACKGROUND

Irrigation is a commonly used method for cleaning open, contaminated and chronic wounds. During irrigation, sterile irrigation fluids act upon wounds to remove lifeless tissue, bacterial inoculum, blood clots, loose dirt and foreign bodies in the vicinity and in the depths of the wound. The critical parameters of any wound irrigation method are the application of an adapted volume of sterile irrigation fluid to the wound and the use of sufficient pressure that must be applied in a precise pattern of distribution for effectively removing the contaminants.

In this context, a disposable nozzle is known from EP 2 251 142 A1 for insertion into a handpiece, where said nozzle produces a highly focused high-pressure micro water jet for the treatment of wounds. Such a high-pressure micro water jet can be used in particular for cleaning, washing and debriding necrotic, wet, or otherwise poorly healing wounds (e.g. caused by diseases such as ulcers, gangrene, bedsores, abscesses or fistulas). The kinetic impact force of the fluid under pressure is there utilized in order to clean the wound and to debride it. In particular debridement, i.e. the restoration of the wound bed by removing necrotic and fibrinous layers, requires the use of an irrigation fluid jet that is operated with high pressure.

However, the high pressure of the fluid jet does not only lead to the removal of the layer or of the particles from the wound, but inevitably also to an aerosol (fluid mist) around the wound composed of droplets of body fluid and irrigation fluid floating in the air. However, aerosols can also be produced in other ways, for example, during wound treatment by way of plasma or ultrasound. In the event that no protective measures are taken, such aerosols can freely escape into the environment and thus pose a significant hazard to patients and/or the respective health care professional.

The high hazard potential of such aerosols is due to the fact that wounds almost always are colonized by pathogens (such as bacteria, viruses or fungi), whereby also the aerosols being produced during their treatment represent a potentially infectious medium because they are laden with pathogens. Consequently, dangerous cross-infection could in the absence of additional protection measures occur between the patients and the individuals present in the treatment room or the individuals later entering the treatment room or the individuals later using the treatment equipment. In addition, free distribution of the aerosol during wound treatment would lead to contamination in the treatment room, in particular of the treatment table and the surrounding floor surfaces. This in turn results in an increased risk of slipping and thereby the risk of injury to individuals in the treatment room. A further problem is the obstruction of the view onto the treatment area when the freely spreading aerosol e.g. collects on the protective glasses of the attending person.

In view of the aforesaid drawbacks, numerous methods and devices are known from prior art to mitigate or even to entirely prevent contamination of the environment by aerosols produced during wound irrigation.

The most common and easiest way is to place the body part of the patient to be treated under a transparent disposable protective foil which can be suspended with the aid of a respective stand device and spanned in a tent-like manner. The respective health care professional dons a protective coat, protective gloves, a protective mask and protective glasses before he reaches either under the protective foil or in respective hand openings provided in the protective foil for performing wound treatment. The treatment fluid draining during the treatment can be collected by way of compresses and/or a good absorbent wound pad.

Such protective foils, however, offer only inadequate protection for the health care professionals and patients from body and irrigation fluids laden with bacteria, viruses, fungi, parasites and/or other pathogens spraying back. Firstly, such pathogens can naturally enter the environment through the two hand openings. Secondly, it is disadvantageous that the gloved hand still needs to reach into the treatment chamber located under the protective foil and contaminated with aerosol. The pathogens can therefore after termination of the treatment enter the environment via gloves and protective clothing, e.g., at control buttons of treatment devices. Also disadvantageous is that the visibility and the splash protection effect are inversely proportional to each other. The more hermetically the wound is covered by the protective foil, the more obstructed the vision of the attending person onto the wound area and vice versa.

Though protective foils with extensions designed as gloves for an attending person to slip into are known, such integrated solutions are disadvantageous, however, in that forcing the hands into or out from then glove extensions proves to be very difficult. In addition, the drawback remains that the attending person must reach into the aerosol-contaminated treatment chamber. Also pathogens (such as e.g. bacteria) can continue to enter the environment through the glove extensions.

Furthermore, suction/irrigation tips are known from prior art which have a generally funnel-shaped splash shield at the front (distal) end in order to prevent irrigation fluid from splashing rearward (cf. for example, U.S. Pat. No. 5,460,604 A). A drawback of such devices is that the motion performed during wound treatment by the suction/irrigation tip must also be carried out by the splash shield that bears snugly on the patient's skin. This motion can by the patient be perceived as being painful. Once the splash shield is lifted from the skin to eliminate this pain, however, the tightness of the treatment chamber formed under the splash shield is also reduced. Dangerous, highly contagious fluid droplets can thereby escape into the environment despite the splash shield.

In addition, systems are known in which a fluid jet device is combined with a suction device for the extraction of the tissue cells separated or dissolved and/or the irrigation fluid.

Such systems, however, are very complex in design since not only fluid supply but also additional extraction (possibly with recirculation of the irrigation fluid) must be present.

BRIEF SUMMARY

The object of the present invention is therefore to provide a protective cover which in a simple manner provides reliable protection against contamination without impairing the effectiveness of wound treatment.

This object is satisfied by a protective cover having the features of claim 1.

The protective cover according to the invention for protection against contamination from body and/or irrigation fluid in the treatment of wounds or ulcers has a first opening to be placed on a body part of a patient and a second opening adapted for the insertion of a handpiece for wound or ulcer treatment. Furthermore, the protective cover of the invention comprises a fluid-tight and flexible hollow body which in the interior defines a treatment chamber having a shape that adapts to the motion of the handpiece, where the hollow body is provided with at least one stiffening element for keeping the first opening in an open state during treatment.

Due to the flexible design of the hollow body, the latter is arbitrarily bendable and adaptable in length. Consequently, the shape of the treatment chamber formed in the interior of the hollow body, i.e. the chamber that connects directly above the wound to be treated and receives the aerosol produced during wound treatment, can be adapted to any motion of the handpiece emitting the irrigation fluid jet. The handpiece can in particular by the doctor or wound specialist be positioned at any distance and any angle to the wound to be treated, without fluid-tightness of the protective cover thereby being impaired. Due to the stiffening element additionally provided in the hollow body, however, the first opening of the protective cover to be placed on the body part of the patient always remains in an unfolded i.e. expanded during every motion of the hand piece. The first opening can therefore with its edge be placed flush on the skin of the patient in order to hermetically enclose the wound to be treated.

The stiffening element can in particular extend over only a part of the length of the protective cover, so that the first opening is formed not directly on the underside of the protective cover, but offset therefrom upwardly. An additional unstiffened material portion (e.g. nonwoven) is therefore present below the first opening and can be stuck under the body part (e.g. the limb) of the patient to close the first opening in a tight manner.

Only the handpiece of the wound cleaning device must for treating wounds advantageously additionally be inserted through the second opening of the protective cover, where the hand of the doctor or other wound specialist guiding the handpiece, however, remains outside the treatment chamber. Potentially infectious contact with the aerosol is thereby avoided.

One advantageous embodiment of the invention provides that at least one inner layer of the hollow body facing the treatment chamber is made of absorbent material, in particular of porous absorbent material for receiving fluid from the aerosol produced during the treatment in the treatment chamber.

The fluid contained in the aerosol is received by the absorbent inner layer and retained therein, so that only relatively little or no fluid can penetrate to the outer layer and the other surfaces of the protective cover, with the advantageous result that pathogens (such as bacteria, viruses and fungi) possibly contained in this fluid are reliably prevented from escaping. The thickness and absorbency of the absorbent layer is dimensioned such that the total fluid volume in the aerosol that is emitted during normal wound treatment duration is reliably absorbed by the absorbent layer without the structural integrity of the absorbent layer there being lost.

It is in a further advantageous embodiment provided that at least one outer layer of the hollow body facing the environment is made of fluid-tight material, in particular fluid-tight plastic, for preventing the contaminated fluid from escaping into the environment.

The fluid possibly escaping through the absorbent inner layer can thereby be reliably retained by the fluid-tight outer layer (e.g. made of polyethylene foil) and prevented from uncontrollably escaping into the environment. It is understood that the hollow body can also be formed having a single layer from material which combines both above requirements (namely absorbency and fluid-tightness), whereby in particular textile barrier materials would there need to be mentioned, for example, microfiber fabric.

According to a particularly advantageous embodiment of the invention, the hollow body is formed having a funnel shape, where its larger opening forms the first opening and its smaller opening is covered with a transparent plate for visually monitoring the treatment area.

The diameter of the funnel-shaped hollow body increases toward the patient, where the hollow body in the first opening surrounding the wound or ulcer reaches its maximum diameter to thereby reliably seal the entire treatment area. Inserted in the opposite opening of the hollow body facing away from the patient is a transparent plate functioning as a window through which the attending person has a clear view onto the treatment area.

According to a further embodiment of the invention, the stiffening element extends around the longitudinal axis of the funnel-shaped hollow body in a helical or circular shape over at least part of the length of its shell.

The helical or circular shape of the stiffening element in particular causes reinforcement in the radial direction in order to keep the two openings of the funnel-shaped hollow body stable in an open state, which is the unfolded or expanded state of the hollow body, so that the lower opening, being larger in diameter, can serve to enclose the treatment area and the upper opening, being smaller in diameter, to see the treatment area. The length of the helically shaped stiffening element is preferably dimensioned such that a projection length of hollow body material with no stiffening remains in the lower region of the hollow body facing the patient, which is loosely placed onto the patient's skin and, if necessary, can also be glued on in order to seal the treatment area in a fluid-tight manner.

Furthermore, it is in an advantageous embodiment of the invention provided that the stiffening element is composed of elastically resilient material, in particular of elastically resilient plastic, the elasticity of which during the treatment allows the compression and expansion of the funnel-shaped hollow body in the direction of its longitudinal axis.

Unlike a rigid spray shield, the protective cover according to the invention makes it possible to vary the distance of the handpiece, emitting the fluid jet, to the treatment area, depending on the wound situation given. The stiffening element there behaves like a low stiff compression spring which is flexible in all directions and compressible or expandable along its length.

According to a particularly advantageous development of the invention, the funnel-shaped hollow body is formed from a web of material that is composed of one or more layers, the ends of which are connected to each other by a seam, where the seam extends in particular along a surface line of the funnel-shaped hollow body.

Fabrication of the hollow body from a single funnel-shaped rolled-up web of material requires only the application of a longitudinal seam for connecting together the two abutting or overlapping ends of the web of material. This can in terms of manufacturing technology be realized in a simple manner and therefore at particularly low costs.

In a further embodiment of this advantageous development, the stiffening element is integrated into the web of material of the funnel-shaped hollow body, in particular glued into and/or welded into and/or sewn into the web of material.

Sewing it in using a sewing machine is in this case particularly advantageous because also dissimilar materials can there be permanently connected to each other. The stiffening element can there be made of material suitable for the respective application, for example, of plastic, in particular plastic fiber and/or made of a fabric material and/or foil material, where each of these materials can easily be sewn to the web of material of the hollow body.

The stiffening element can be disposed between an inner and an outer layer of the web of material of the funnel-shaped hollow body, whereby reliable and stationary positioning of the stiffening element protected against external influences is obtained.

An embodiment of the invention is illustrated in the figure and shall be described in more detail below.

DETAILED DESCRIPTION

Figure 1:
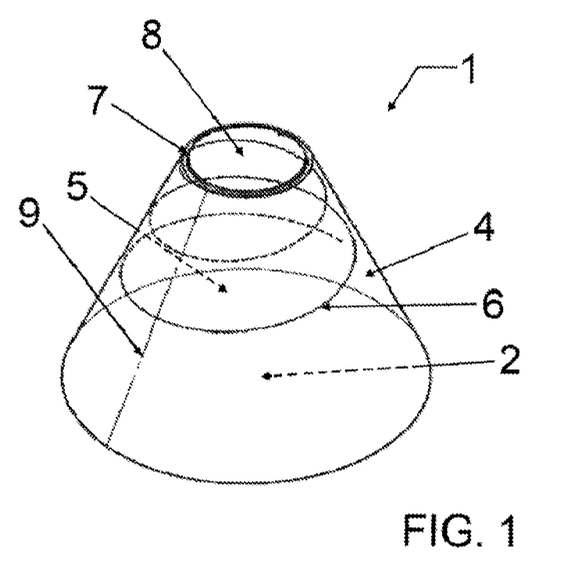
FIG. 1 shows an overall perspective view of a preferred embodiment of a protective cover according to the invention.
Figure 2:
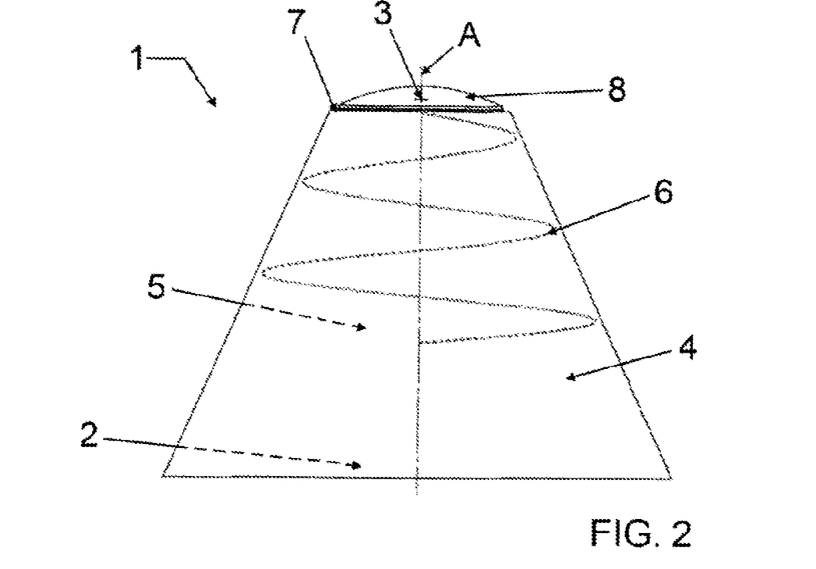
FIG. 2 shows a side view of the protective cover of FIG. 1.
Figure 3:
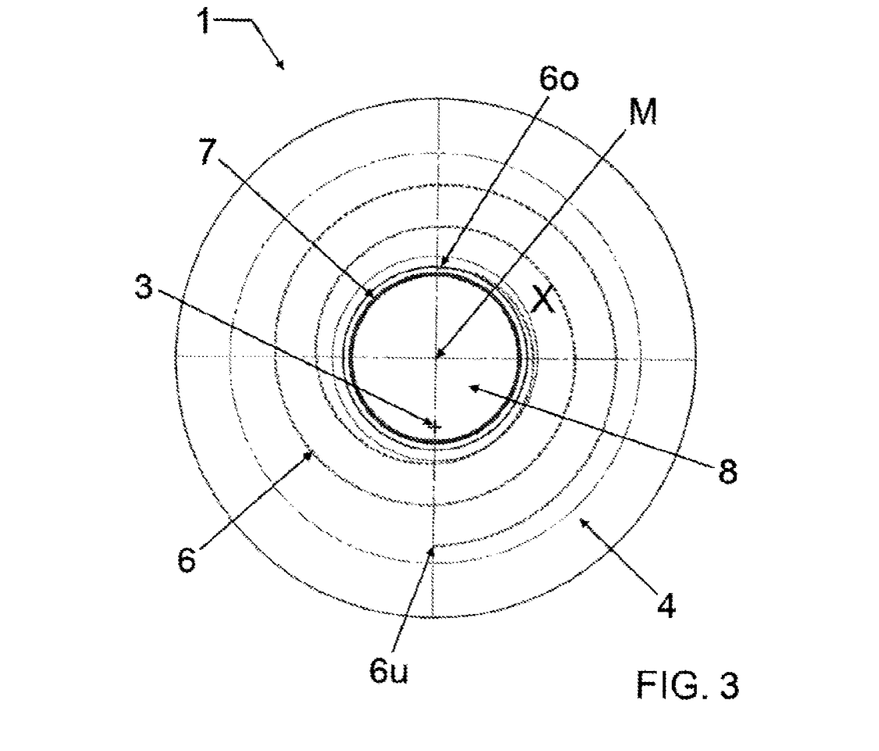
FIG. 3 shows a top view of the protective cover of FIG. 1.

Protective cover 1 according to the invention illustrated in FIGS. 1, 2 and 3 respectively in an overall view in its non-deformed initial state has a shape resembling a jellyfish. The core component of protective cover 1 is there formed by an axially symmetric funnel-shaped hollow body 4 which along its longitudinal axis A comprises two openings 2, 7 which are in turn arranged axially and diametrically opposite to one another, where these openings 2, 7 are of different size.

Larger opening 2, in FIGS. 1 and 2 respectively facing downwardly, is in the later use placed on a body part of a patient, generally a limb, where the edges of opening 2 define a treatment area in which a wound to be treated with an irrigation fluid jet or other skin disorders of the patient (e.g. an ulcer) is located.

Hollow body 4 encloses a frustoconical interior which in later use acts as a treatment chamber 5 into which the head end (not shown) of a handpiece is introduced, from which in turn an irrigation fluid jet is emitted for treating wounds (wound irrigation and optionally wound debridement). The handpiece is for this purpose outside of treatment chamber 5 via a hose connected to an irrigation fluid reservoir for supplying pressurized irrigation fluid (e.g. sterile water or a saline solution).

The handpiece, however, can also be any part of a wound treatment device that is for local wound treatment movable by hand. For example, plasma or ultrasonic waves can also be emitted from the handpiece for wound treatment instead of the irrigation fluid jet. It is only crucial that aerosol harmful to health forms during the treatment of wounds using the handpiece and requires shielding.

In order to, firstly, seal treatment chamber 5 in a fluid-tight manner toward the top and, secondly, to enable the attending person a clear view onto the treatment area bordered by the oppositely disposed lower opening 2, the smaller opening 7 of the funnel-like hollow body 4 in FIGS. 1 and 2 respectively facing upwardly is covered with a circular rigid plate 8 made of transparent material, e.g. made of transparent plastic such as polymethylmethacrylate (PMMA). Plate 8—as clearly visible in the enlarged top view of FIG. 4—is by way of a circular circumferential seam 10, which, for example, can be mechanically produced by a sewing machine, connected to the upper opening edge of hollow body 4. However, it would alternatively also be conceivable to place plate 8 only loosely onto smaller opening 7. In such a case, plate 8 could as a disposable item after each treatment of wounds be disposed of separately from hollow body 4.

As is apparent from FIG. 2, plate 8 has a bowl-like curved shaped that is convex outwardly, where the curvature of the plate can cause a magnifying glass effect in order to be able to see the wound to be treated more closely. In addition, it can with such a plate curvature be prevented that fluid droplets obstructing the view can accumulate.

Figure 4:
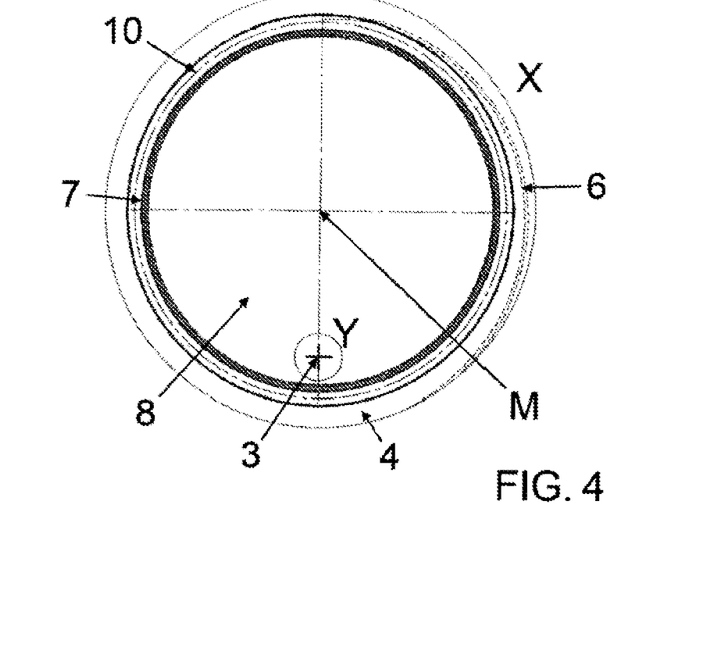
FIG. 4 shows an enlarged top view of the protective cover in the region "X" of FIG. 3.
Figure 5:
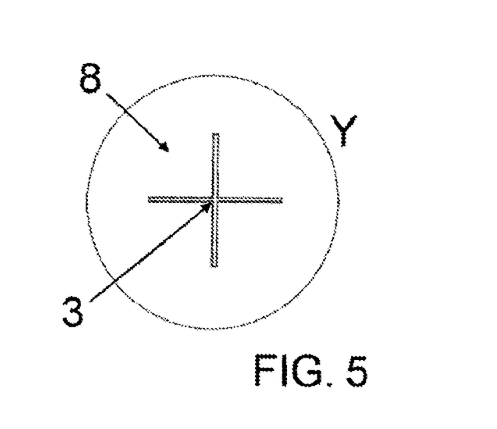
FIG. 5 shows an enlarged top view of the protective cover in the region "Y" of FIG. 4.

As is evident in particular in the enlarged views of FIGS. 4 and 5, transparent plate 8 comprises an opening in the form of a cross recess 3 disposed eccentrically, i.e. laterally offset from center M of plate 8 which is in alignment with the longitudinal axis A of hollow body 4. This cross recess 3 is used for insertion of a handpiece for treating wounds (e.g. a handpiece emitting an irrigation fluid jet, plasma, or ultrasonic waves) and is in the plan view of FIG. 4 illustrated with an arrangement located vertically below the plate center M. In later use, however, protective cover 1 can be turned such that cross recess 3 assumes a position that is pleasant for the attending person when inserting and handling the handpiece. A right hander will therefore generally twist protective cover 1 about its longitudinal axis A such that cross recess 3 is from his perspective located to the right of longitudinal axis A and plate center M.

The recess widths of cross recess 3 are preferably approximately 0.5 mm. The head end of the handpiece is inserted at the intersection of the two recesses, whereby cross recess 3 initially expands elastically. Once the head end has been introduced into treatment chamber 5, cross recess 3 again bears against the outer perimeter of the handpiece in a fluid-tight manner such that no contaminated fluid can escape between cross recess 3 and the handpiece.

The attending person must advance the handpiece only to such a degree through cross recess 3 of plate 8 that the nozzle arranged at the head end of the handpiece is positioned within treatment chamber 5 (below plate 8). However, the remaining part of the handpiece remains outside treatment chamber 5 (above plate 8) in order to be moved, for example, by way of a handle used by the hand of the attending person for the purpose of performing wound treatment. Since directing the irrigation fluid jet is thereby effected by a part of the handpiece disposed above plate 8 and as a free view to the fluid jet generated below plate 8 and the wound is at the same time given, the attending person must no longer with his hands enter the aerosol-contaminated treatment chamber 5. This risk of infection is thereby significantly reduced. This advantageous effect is also obtainable when the opening (cross recess 3) is for insertion of the hand piece not—as shown in FIG. 3—formed in plate 8, but instead in hollow body 4. In such a case, plate 8 would serve as a pure viewing window.

In addition to the embodiment shown, however, it is also conceivable to provide hand openings laterally in hollow body 4 through which a gloved hand can in case of need reach into treatment chamber 5 in order to, for example, collect treatment fluid draining during wound treatment by use of compresses or swabs. These hand openings can additionally be fitted integrated gloves. It is there important that irrigation fluid can escape from treatment chamber 5 neither in the region of the hand openings nor in the region of the gloves that are possibly integrated there. In addition, straps can be formed at the side on hollow body 4 for raising protective cover 1 as a whole or possibly suspend it in the unused state.

A large potential hazard emanates from the aerosols that are produced during wound treatment due to the high impact pressure of the irrigation fluid jet. Due to the bacterial, viral, fungal or parasitic content of most wounds, these aerosols are in fact usually highly contagious. In addition, the resulting aerosol affects the unobstructed view onto the treatment area, thereby making it difficult for the attending person to precisely recognize the wound treatment progress.

It is consequently to be required of the material of hollow body 4 that, firstly, it exhibits sufficient absorbency to absorb and retain the fluid droplets produced during wound treatment in treatment chamber 5. It is there sufficient to merely provide the inner layer of hollow body 4 facing treatment chamber 5 with absorbent material. Paper, textile or nonwoven fabric can be used as absorbent material. These materials have the advantageous property that saturation of the absorption capacity is not reached even after long duration of treatment and that therefore the adsorption by surface wetting can act throughout the entire treatment period. This adsorption acts as a driving force which binds the fluid-bound pathogens (such as bacteria) to the fibers of the paper, textile or nonwoven. The small droplets laden with pathogens are there quickly and successfully absorbed and retained by the paper, fabric or non-woven. With an increasing amount of fluid bound in the paper, fabric or nonwoven, the fluid-soaked surface enlarges and the adsorption effect can even be accelerated.

Fluid-tightness in addition to absorbency is secondly required of the material of hollow body 4 to reliably prevent the body and irrigation fluid droplets that are during the wound treatment flung into treatment chamber 5 and mixed with highly contagious ichor, from escaping into the environment and to thereby avoid contamination of the environment. It is for this purpose sufficient to have at least one outer layer, i.e. a layer facing away from treatment chamber 5, of hollow body 4 be made of fluid-tight material, e.g. fluid-tight plastic foil.

A preferred multi-layer material for hollow body 4 that satisfies the above-described properties in terms of absorbency and fluid-tightness has a polyethylene foil as an outer layer and one or two layers of cellulose as an inner layer.

When using the aforementioned material, however, the fundamental problem exists that it has no or only low inherent stability. Like a disposable protective foil commonly used for patient coverage, such material would collapse upon itself if no additional stiffening measures were taken. It must in particular be ensured that lower opening 2 on the patient body for enclosing the wound is at all times kept in an unfolded or expanded state. Only in this manner can it be ensured that the hollow body material can not enter the patient's wound or in the field of view of the attending person.

In order to obtain—as shown in FIGS. 1 and 2—stable installation of protective cover 1 with a lower opening 2 permanently held in the unfolded or open position, stiffening element 6 is provided counteracting deformation of hollow body 4 in the radial and axial directions, which is in accordance with the overall views shown in FIGS. 1 and 2 formed as a plastic wire (having a diameter of, for example, 2 mm) extending helically with two and a half turns about the longitudinal axis.

The helical stiffening element 6 is integrated into the material of hollow body 4, where this integration can be effected e.g. by stiffening element 6 being sewn in. This integration can be effected in a fixed or detachable manner. In the latter case, stiffening element 6 can e.g. only be inserted or clicked into the material of hollow body 4. Dissimilar materials can be connected together easily by sewing, for which reasons stiffening element 6 can instead of plastic also be made of any other desired material having a reinforcement effect, e.g. metal. Stiffening element 6 must also not necessarily be given in wire form, but can also be of any other form that is integrated in hollow body 4, e.g. foil form. With a multi-layered hollow body 4, stiffening element 6 is preferably arranged between the layers. Such an embedded arrangement has the advantage that stiffening element 6 is protected against external influences, such as aerosol produced during wound treatment, and that particularly stable positioning of stiffening element 6 in hollow body 4 is additionally obtained.

In the plan view of FIG. 3, stiffening element 6 extends helically around center M of plate 8 which is arranged in extension of longitudinal axis A. Upper end point 6*o*—as seen in the longitudinal direction—of stiffening element 6 and lower end point 6*u*—as seen in the longitudinal direction—of stiffening element 6 are in relation to center point M of plate 8 arranged diametrically opposite to one another, wherein cross recess 3 for the insertion of the handpiece emitting the fluid jet is located on the line connecting these two end points 6*o*, 6*u*.

Despite the provision of stiffening element 6, flexibility of hollow body 4 is nevertheless maintained and allows adapting the shape of treatment chamber 5 defined in the interior of hollow body 4 to any arbitrary motion of the handpiece. Stiffening element 6 has deformation properties similar to a low compression spring with a high pitch. Accordingly, hollow body 4 with integrated stiffening element 6 can continue to be bent freely to all sides and also be compressed and expended in the longitudinal direction. These deformation properties allow positioning the handpiece during wound treatment at any angle and/or at any distance to the wound to be treated.

The attending person will for this during wound treatment exert a deforming force upon hollow body 4 via a free hand and/or directly via the handpiece inserted in cross recess 3 in order to adapt the shape of hollow body 4 and treatment chamber 5 defined by it to a new position of the handpiece. Irrespective of this, however, fluid-tightness of treatment chamber 5 is maintained at all times. Treatment chamber 5 is namely—irrespective of the shape just adopted—always closed in a fluid-tight manner toward the top by plate 8 and toward all sides by the shell of hollow body 4.

The reinforcement effect in the radial and the axial direction of hollow body 4 achieved by integrated stiffening element 6, however, advantageously leads to hollow body 4 at all times having a stable open lower opening 2 regardless of its current shape adapted to the motion of the handpiece. Stiffening element 6 therefore opens i.e. expands the treatment chamber 5. It is during use sufficient to hold protective cover 1 with a free hand, e.g. at the edge of plate 8. However, manually holding protective cover 1 can also be dispensed with entirely, as the latter is already fixed by the handpiece that has been pushed into cross recess 3. Both hands of the doctor or other wound specialist are therefore advantageously available for wound treatment.

Due to the compressibility of hollow body 4 given in the direction of longitudinal axis A, it is with slight manual pressure possible to place protective cover 1 in a flush manner on any body part of a patient. The shape of the lower side of protective cover 1 is thereby optimally adapted to the shape of the respective body part, thereby reducing the risk of leakage between the patient body and protective cover 1 to a minimum. In addition, protective cover 1 can due to the compressibility of hollow body 4 be squeezed together for shipping and storage purposes almost flat to possibly be inserted into a respective wrapper.

Hollow body 4 is in terms of manufacturing technology configured in a particularly simple and therefore cost-effective manner as it consists only of a single web of material. In order to form hollow body 4, an arcuate web of material is rolled up such that the two opposite ends of the web of material come to rest on one another overlapping each other and are then sewn with a thread. Such an overlap seam 9 is basically more durable than an edge-to-edge configuration and also tends to be easier to manufacture. Overlap seam 9 is in the final protective cover 1 located on the inner side toward treatment chamber 5 in order not to affect tightness and the overall visual impression of hollow body 4. In the non-deformed initial state of protective cover 1 according to FIG. 1, overlap seam 9 extends along a surface line of funnel-shaped hollow body 4.

Helical stiffening element 6—as seen in the direction of longitudinal axis A—does not extend over the entire length of hollow body 4. Though stiffening element 6 starts almost flush at the upper edge of hollow body 4 covered by plate 8, it terminates at a significant distance to the lower edge of hollow body 4. The length of stiffening element 6 measured in the direction of longitudinal axis A assumes a value relative to the overall length of hollow body 4 of approx. ½ to ¾, preferably approx. ⅔. Accordingly, there is a lower longitudinal section of hollow body 4 only made of a non-reinforced web of material (without integrated stiffening element 6). This lower longitudinal section can in later use be fitted loosely on the patient's body and optionally also be glued on to create a tight closure downwardly between the patient's body and protective cover 1.

Protective cover 1 according to the invention can be advantageously employed in any device for irrigating wounds or ulcers. It can in particular be part of a device for debriding necrotic body tissue by way of a micro water jet. In such a device, a hand-operated lance is used as a hand device, where this lance is inserted into cross recess 3 of protective cover 1 so far that the nozzle disposed on the free end of the lance for generating the micro water jet is located within treatment chamber 5. Use of protective cover 1 according to the invention achieves high safety from contamination of the environment with body and/or irrigation fluid during the wound debridement, however, without the freedom of movement of the handpiece and the vision of the attending person onto the wound to be debrided and the micro-water jet being obstructed

What is claimed is:

1. A protective cover for protection against contamination from body and/or irrigation fluid during treatment of wounds or ulcers, said protective cover comprising: a first opening to be placed on a body part of a patient; and a second opening adapted for insertion of a handpiece for wound or ulcer treatment, wherein said protective cover comprises a hollow body that is fluid-tight and flexible, and which in an interior defines a treatment chamber having a shape that adapts to a motion of said handpiece; said hollow body is provided with at least one stiffening element for keeping said first opening in an open state during treatment; and said stiffening element extends around a longitudinal axis of said hollow body in a helical shape over at least part of a length of its shell; wherein said hollow body is formed having a funnel shape, where its larger opening forms said first opening and its smaller opening is covered with a transparent plate for visually monitoring a treatment area; and wherein said stiffening element is composed of elastically resilient material, in particular of elastically resilient plastic, the elasticity of which during the treatment allows compression and expansion of said funnel-shaped hollow body in the direction of its longitudinal axis.

2. The protective cover according to claim 1, wherein at least one inner layer of said hollow body facing said treatment chamber is made of absorbent material, in particular of porous absorbent material, for receiving fluid from an aerosol produced during the treatment in said treatment chamber.

3. The protective cover according to claim 1, wherein at least one outer layer of said hollow body facing an environment is made of fluid-tight material, in particular fluid-tight plastic, for preventing the contaminated fluid from escaping into the environment.

4. The protective cover according to claim 1, wherein said funnel-shaped hollow body is formed from a web of material that is composed of one or more layers, ends of which are connected to each other by a seam, where said seam extends in particular along a surface line of said funnel-shaped hollow body.

5. The protective cover according to claim 4, wherein said stiffening element is integrated into said web of material of said funnel-shaped hollow body, in particular glued into and/or welded into and/or sewn into said web of material.

6. The protective cover according to claim 1, wherein said transparent plate is loosely fitted in order to be disposed of as a disposable item after the wound treatment has been completed; wherein said transparent plate is connected to said funnel-shaped hollow body by a circular circumferential seam; wherein said transparent plate is configured as a convex curved plate, the curvature of which is directed outwardly away from said treatment chamber; and wherein said transparent plate is made of rigid material, in particular rigid plastic or glass, where said second opening is provided in said transparent plate.

7. The protective cover according to claim 6, where said second opening is configured such that it expands radially upon insertion of said handpiece and after completion of the insertion bears substantially in a fluid-tight manner against the outer perimeter of said handpiece.

8. A protective cover for protection against contamination from body and/or irrigation fluid during treatment of wounds or ulcers, said protective cover comprising: a first opening to be placed on a body part of a patient; a second opening adapted for insertion of a handpiece for wound or ulcer treatment, wherein said protective cover comprises a hollow body that is fluid-tight and flexible, and which in an interior defines a treatment chamber having a shape that adapts to a motion of said handpiece; the hollow body is formed from a web of material that is composed of one or more layers, ends of which are connected to each other by a seam; and said hollow body is provided with at least one stiffening element for keeping said first opening in an open state during treatment wherein said hollow body is formed having a funnel shape, where its larger opening forms said first opening and its smaller opening is covered with a transparent plate for visually monitoring a treatment area; and wherein said stiffening element is composed of elastically resilient material, in particular of elastically resilient plastic, the elasticity of which during the treatment allows the compression and expansion of said funnel-shaped hollow body in the direction of its longitudinal axis.

9. The protective cover according to claim 8, wherein at least one inner layer of said hollow body facing said treatment chamber is made of absorbent material, in particular of porous absorbent material, for receiving fluid from the aerosol produced during the treatment in said treatment chamber and where at least one outer layer of said hollow body facing the environment is made of fluid-tight material, in particular fluid-tight plastic, for preventing the contaminated fluid from escaping into the environment.

10. The protective cover according to claim 9, wherein said stiffening element is integrated into said web of material of said hollow body and is disposed between an inner and an outer layer of said web of material of said funnel-shaped hollow body.

11. The protective cover according to claim 9, wherein said stiffening element extends around the longitudinal axis of said funnel-shaped hollow body in a helical shape over the entire length of its shell.

12. The protective cover according to claim 11, wherein said stiffening element is composed of elastically resilient material, in particular of elastically resilient plastic, the elasticity of which during the treatment allows the compression and expansion of said funnel-shaped hollow body in the direction of its longitudinal axis.

13. A protective cover for protection against contamination from body and/or irrigation fluid during treatment of wounds or ulcers, said protective cover comprising: a first opening to be placed on a body part of a patient; and a second opening adapted for insertion of a handpiece for wound or ulcer treatment, wherein said protective cover comprises a hollow body that is fluid-tight and flexible, and which in an interior defines a treatment chamber having a shape that adapts to a motion of said handpiece; said hollow body is provided with at least one stiffening element for keeping said first opening in an open state during treatment; and said second opening is covered with a transparent plate for visually monitoring a treatment area; and said transparent plate is configured as a convex curved plate, a curvature of which is directed outwardly away from said treatment chamber; and wherein said stiffening element is composed of elastically resilient material, in particular of elastically resilient plastic, the elasticity of which during the treatment allows the compression and expansion of said hollow body in the direction of its longitudinal axis.

14. The protective cover according to claim 13, wherein said transparent plate is loosely fitted in order to be disposed of as a disposable item after the wound treatment has been completed.

15. The protective cover according to claim 14, wherein said transparent plate is connected to said hollow body by a circular circumferential seam.

16. The protective cover according to claim 14, wherein said second opening is configured such that it expands radially upon insertion of said handpiece and after completion of the insertion bears substantially in a fluid-tight manner against the outer perimeter of said handpiece.

17. The protective cover according to claim 16, where said hollow body has a funnel shape, where its larger opening forms said first opening and its smaller opening said second opening and where said stiffening element extends around the longitudinal axis of said funnel-shaped hollow body in a helical or circular shape over at least part of the length of its shell.

18. The protective cover according to claim 13, wherein said transparent plate is made of rigid material, and said second opening is provided in said transparent plate.

* * * * *